(12) United States Patent
Shelhamer et al.

(10) Patent No.: US 7,967,439 B2
(45) Date of Patent: Jun. 28, 2011

(54) WIRELESS SCLERAL SEARCH COIL INCLUDING SYSTEMS FOR MEASURING EYE MOVEMENT AND METHODS RELATED THERETO

(75) Inventors: Mark John Shelhamer, Reisterstown, MD (US); Dale Charles Roberts, Halethorpe, MD (US)

(73) Assignee: The Johns Hopkins University, Baltimore, MD (US)

( * ) Notice: Subject to any disclaimer, the term of this patent is extended or adjusted under 35 U.S.C. 154(b) by 137 days.

(21) Appl. No.: 11/920,808

(22) PCT Filed: May 19, 2006

(86) PCT No.: PCT/US2006/019578
§ 371 (c)(1), (2), (4) Date: Apr. 17, 2009

(87) PCT Pub. No.: WO2006/125185
PCT Pub. Date: Nov. 23, 2006

(65) Prior Publication Data
US 2010/0045932 A1    Feb. 25, 2010

Related U.S. Application Data

(60) Provisional application No. 60/682,731, filed on May 19, 2005.

(51) Int. Cl.
*A61B 3/14* (2006.01)
(52) U.S. Cl. .................. 351/209; 351/212; 351/247
(58) Field of Classification Search .............. 351/205, 351/209, 210, 212, 219, 246, 247; 600/399, 600/409, 410, 422–424
See application file for complete search history.

(56) References Cited

U.S. PATENT DOCUMENTS

| | | |
|---|---|---|
| 6,579,235 B1 | 6/2003 | Abita et al. |
| 7,041,063 B2 * | 5/2006 | Abreu .................. 600/549 |
| 2004/0207808 A1 | 10/2004 | Fleischman et al. |

* cited by examiner

*Primary Examiner* — Huy K Mai
(74) *Attorney, Agent, or Firm* — Edwards Angell Palmer & Dodge LLP; Peter F. Corless; William J. Daley, Jr.

(57) ABSTRACT

Featured is a wireless scleral search coil that includes one or more passive, resonant coils and in a particular embodiment two orthogonal, passive, resonant coils, where each coil resonates at a different frequency. Each resonant coil includes a coil-capacitor circuit, each circuit being configured to resonant at a different frequency. Such a wireless scleral search coil is disposed within a biocompatible material that is shaped to conform and rest upon the eye of a subject. Also featured are system including such a wireless scleral search coil, one or more transmitter coils, an assembly of one or more receiver coils and a calculating sub-system for processing signal data to obtain eye measurement information.

32 Claims, 9 Drawing Sheets

WIRELESS SCLERAL SEARCH COIL INCLUDING SYSTEMS FOR MEASURING EYE MOVEMENT AND METHODS RELATED THERETO This application claims the benefit of U.S. Provisional Application Ser. No. 60/682,731 filed May 19, 2005, the teachings of which are incorporated herein by reference.

STATEMENT REGARDING FEDERALLY-SPONSORED RESEARCH

The present invention was supported by grants from the National Science Foundation (NSF), grant number DBI-9876635 and the National Institute of Health (NIH/MIBIB), grant number R)1 EB001914. The U.S. Government may have certain rights to the present invention.

FIELD OF INVENTION

The present invention generally relates to devices, systems and methods for measurement of eye movement, more particularly to devices, systems and methods embodying a scleral search coil and yet more particularly to devices, systems and methods embodying a wireless scleral search coil.

BACKGROUND OF THE INVENTION

The control of eye movements represents one of the most basic and fundamental motor control systems of the human brain, combining information from both low-level motion transducers in the inner ear (vestibular system) and high level-visual information. The measurement of eye movements has become an important tool in probing some higher-level cognitive functions, including reading, learning, prediction, memory, and direction of attention. Understanding and developing neural models of eye movement control systems is helpful not only to the clinical neurologist in aiding with the diagnosis and localization of functional deficits, but also to the wider neurological research community in contributing to the general understanding of how the human brain directs visual attention and controls motor systems. As more is learned about how the various parts of the brain operate and interact, precise measurement of eye movements has been called on more and more to provide both direct and indirect assessment of vestibular, oculomotor, visual, and neurologic function. To this end, increasingly sophisticated experiments and more inexpensive and versatile equipment have been developed.

There are a number of widely used methods for measuring eye position, each with its own benefits and drawbacks. One of the most popular methods used for the eye measurement is the scleral search coil system, developed by David A. Robinson (Robinson DA. A method of measuring eye movement using a scleral search coil in a magnetic field. *IEEE Trans Biomed Electron* 1963; BME-10: 137-145). Among its benefits are high resolution and accuracy, low noise, fast response (wide bandwidth), wide range, cost effectiveness, ease of use, and ability to measure torsional eye movements (rotations about the line of sight).

In existing systems embodying such methods, a contact lens containing one or two coils of wire is placed on the subject's eye or the coil(s) is surgically implanted for animal studies. The coils on the contact lens are connected to electronic amplifiers through fine wires that extend from the lens. The subject sits inside a set of large coils that generate relatively homogeneous AC magnetic fields. These magnetic fields induce current in the coil on the eye, which are detected and amplified and typically sampled by a computer. Since the magnitude of the signal induced into the eye coil is proportional to the sine of the angle between the plane of the eye coil and that of each magnetic field, one can deduce the orientation of the eye from the magnitudes of the received signals.

There are many variations on the search coil system. Such systems can use anywhere from one to three generated magnetic fields, and one or two coils on the eye. Using a single coil on the eye with its plane perpendicular to the line of sight, it is possible to deduce the direction of gaze (i.e., the horizontal and vertical position of the eye). When a second coil perpendicular to the first coil is provided, it is possible to deduce the amount of torsional rotation about the line of sight. In sum, the original search coil system has been in use since the early 1960s with only minor modification and it continues to be widely used when detailed and precise eye movement information is required. Although the scleral search coil system is presently considered the standard, it is not without its limitations as described below.

As indicated above, a wire extends from the lens/coil assembly to the instrumentation. This wire is delicate and is a major source of coil defects. It is not uncommon, especially in a subject who blinks often while making eye movements, for the wire to break at the interface with the lens/coil.

Also, this wire is a source of discomfort for the subject as it rubs the edges and inner surfaces of the eyelids and may become entangled in the eyelashes. In addition, this wire can contribute to motion artifacts, since the eyelids can push the wire and, therefore, move the coil and lens on the eye (Bergamin O, Roberts D C, Ramat S, Straumann D, Zee D Z. Influence of orientation of exiting wire of search coil annuli on torsion following saccades. *AR VO Abstracts* 2003).

The wired scleral contact lenses used in humans are fragile and expensive and typically last for only a few recording sessions. Experiments typically call for a coil on each eye, so a continuous and costly supply of these lenses must be maintained. Further, wire breakage during experiments causes delays, loss of data, and sometimes, due to time constraints, early termination of the experiment.

Surgically implanted coils used in animal studies are extremely expensive due to their risky and labor intensive nature and are also susceptible to breakage. The wire must extend from the eye, under the skin, to a connector on the animal's head. This is an added source of infection and malfunction. Rubbing of the wire inside the animal's head can be a source of discomfort and infection. The mechanical load of the wire can also cause eye movement problems and strabismus.

The standard system using scleral search coils also employs a large cubical frame to hold the field-generating coils, ranging from one to two meters for humans, to several tens of centimeters for smaller animals. An example of a such a cubical frame for human use is shown in FIG. 1. For accurate recordings the eyes must remain near the center of the cube, and thus, the head must be fixed with respect to the surrounding field coils. Also, less head and body movement is allowed as the size of the cube gets smaller. This is such a great restriction that as a general rule, no practical attempt is made to make head-free measurements while using search coils.

The large field coil structure also imposes limits on the location of coil experiments. Typically, such coil systems are not portable. The field coils are usually permanently mounted to a chair or other object in which the subject is confined. Thus, the person or subject must be in the chair or other object and remain in that chair during the entirety of the procedure.

As indicated above, once in the chair the movement of the subject also is usually severally limited. All of this severely restricts the use of search coil systems in novel locations, situations, and orientations.

Another potential problem with existing search coil systems is slippage of the contact lens in human subjects, especially torsionally. Torsional slippage is usually reported during blinks (Teiwes W, Merfeld D M, Young L R, Clarke A H. Comparison of the scleral search coil and video-oculography techniques for three-dimensional eye movement measurement. In: Three-dimensional kinematics of eye, head, and limb movements, M Fetter et al. (eds.), Harwood Academic Publishers, Amsterdam, 1997), indicating that lens slippage may be due to the eyelids pressing on the protruding wire.

Another major confounding effect is that scleral coils seem to change the neural command signal to the extraocular muscles (Frens M A, van der Geest J N. Scleral search coils influence saccade dynamics. *J Neurophysiol* 2002; 88:692-698). For example, saccades are longer and slower when coils are worn (though the effects are each less than 10%). Furthermore, this occurs in both eyes even with a coil in only one eye, so it is not a purely mechanical phenomenon. Without being bound to any particular theory, it is believed that some of this effect may be due to irritation of the eyes from the coils, and in particular from the connecting wires leading from the scleral coils as this is almost always the part of the coils that cause the most discomfort and "awareness" of something in the eye. An ill-positioned connecting wire tends to slide across the lower lid or the lashes, which can be quite annoying and could easily lead to a desire to reduce eye velocity and the duration of eye movements.)

The disadvantage of the wire running from the scleral eye coil to the instrumentation has been recognized by several groups. One approach taken for a search coil that does not use an interconnecting wire that has been proposed (Bour L J, van Gisbergen J A. The double magnetic induction method for measuring eye movement-results in monkey and man. *IEEE Trans Biomed Eng* 1984; 31:419-27; Bos J E, Reulen J P H, Boersma H J, Ditters B J. Theory of double magnetic induction (DMI) for measuring eye movements: correction for nonlinearity and simple calibration in two dimensions. *IEEE Trans Biomed Eng* 1988; 35:733-9; Reulen J P, Bakker L. The measurement of eye movement using double magnetic induction. *IEEE Trans Biomed Eng* 1982; 29:1404), embodies a methodology that relies on the double magnetic induction (DMI) property of conductors in a magnetic field. It uses a simple short-circuited loop of wire (or a metal ring) on the eye. An external magnetic field (the primary field) induces a current in the loop on the eye. The loop on the eye, in turn, generates its own magnetic field (the secondary field), which is detected by a second detector near the eye.

The secondary magnetic field emanating from the shorted eye coil is of the same frequency as, but in phase quadrature to, the primary magnetic field (i.e., they are 90° out of phase), making it possible to sense and detect the secondary field in the presence of the primary field by using a phase-sensitive detector. This elegant solution is useful only for horizontal and vertical eye movements, and cannot be easily extended to include torsional measurements. Small movements of the eye relative to the secondary detector coil cause large errors in the measurements. The DMI system still constrains the subject's position within a large field coil frame. Moreover, these systems have seen only very limited use in a few labs.

Other commercial devices currently in use for the measurement of eye movements include electrooculography (BOG), the infrared (IR) eye tracker, and the video eye tracker (also called VOG for videooculography). BOG, which uses electrodes placed near the eyes, is relatively easy to use, but suffers from lack of sensitivity due to muscle noise, drift due to changes in the skin-electrode interface, and changes in gain and bias due to changes in corneo-retinal potential with variations in ambient lighting. EOG is unsuitable when high resolution and accuracy are required, it cannot measure torsion, and it provides poor vertical measurements. The IR (infra-red light reflection) monitor is easy to use and is insensitive to muscle artifact. However, most IR tracker systems cannot accurately measure eye movements greater than approximately ±15 to ±20 degrees horizontally, and less vertically. These systems also can be difficult to calibrate, and do not measure torsion.

VOG based systems use a small camera and digital image processing hardware and software to compute the eye's orientation. Most systems limit the sample rate to 50 or 60 Hz, though some newer systems are beginning to use digital cameras with higher sampling rates. No video based system today approaches the search coil's ability to measure horizontal, vertical, and torsional eye movements at 1000 Hz and above.

In addition to these limitations, an inherent limitation of VOG is that a camera needs to acquire an image of the eye, and in some situations this maybe difficult or impossible. Droopy eyelids or narrow eye openings cause problems for VOG, as do blinking, squinting, and, obviously, closed eyes. Wearing glasses is not permitted with many types of VOG systems, and patching or occluding an eye may not be permitted. A camera, or some form of optics or right angle prisms, must always be in the field of view, which can be unacceptable in many circumstances. The use of a stereoscopic video apparatus to present visual stimuli (VR: virtual reality) would present a problem, unless the apparatus was specifically designed to accommodate VOG.

There are also several very common experimental setups in which a video system is inconvenient or unacceptable. It is not uncommon to evaluate patients with fourth nerve palsies, which cause the eyes to be misaligned. Part of the testing procedure involves having the patient look at various targets while the right and left eyes are alternately covered, and the positions of both eyes are continuously monitored. This may be problematic because, depending on the configuration of the particular VOG system, covering of the eye may preclude the recording of its position. Another set of experiments requires the subject to wear thin prisms which alter the angle of the image reaching the eye. Video systems would at the least complicate the determination of eye position, or at worst not be usable at all.

Illumination of the eye is required for the camera to capture an image, however, many evaluations require absolute darkness so that the subject has no fixation targets. While infrared illumination results in decreased visibility of the illumination, it may not eliminate it. IR LEDs are sometimes visible as a dim red glow to a subject that is dark adapted, and this can compromise the conditions of the evaluation.

In addition, it can be very difficult to get an image of the eye that is good enough to perform torsional eye movement analysis. Proper torsional analysis requires not just a sharp image of the pupil (which is relatively easy to acquire), but a sharp image of other features of the eye (e.g., the iris) that will allow automatic tracking of torsional movements. The quality of the image can depend on the color of the iris, and the shape of the eyelids affects how much of the iris is visible, so the quality of torsional movements can vary widely between subjects. Proper illumination also is important in obtaining a good iris image. Higher-wavelength IR illumination is less visible to the subject, but it also results in a more washed-out (lower contrast) image of the iris, leading to poorer torsional tracking.

Another shortcoming with VOG is the need to mount the imaging camera to the subject's head, possibly interfering with head motion. Furthermore, if the camera is not very firmly attached, jitter in the resulting image will degrade the quality of the measurement. This is a significant problem that severely restricts the use of video in situations where free and rapid head and body motions occur. The more effective methods to stabilize the device on the head are also quite uncomfortable, requiring a biteboard or clamping to the head.

It thus would be desirable to provide a new scleral search coil including system and methods related thereto which would overcome the shortcomings of the prior art device that uses wires to interconnect the coil to the instrumentation. It would be particularly desirable to provide such a coil, systems and method that would allow the coils and systems to be portable and thus capable of being used in other than a confined subject situation as when using known scleral search coils and related systems. Such search coils preferably would be simple in construction and less costly than prior art scleral search coils.

SUMMARY OF THE INVENTION

The present invention features a wireless scleral search coil and search coil systems and methods that embody or use such a scleral search coil. In regards to the present invention, the term "wireless" is an indication that a wire(s) is not required to connect the coil assembly to instrumentation that is external to the eye. It is envisioned that the coil assembly embodied in the wireless scleral coil of the present invention would include a wire in its structure.

A "wireless" scleral search coil or wireless search coil assembly according to the present invention includes one or more, passive, resonant coils, where each of the one or more coils resonate at a different frequency. In particular embodiments, the wireless scleral search coil or wireless search coil assembly embodies two approximately orthogonal, passive, resonant coils. In further embodiments, each of the resonant coils includes a coil or wire and capacitor circuit, each such circuit being configured to resonant at a different frequency. In yet further embodiments, such a wireless scleral search coil or wireless search coil assembly is disposed within a biocompatible material that is shaped to confirm and rest upon the eye of a subject.

A system embodying such a wireless search scleral coil or search coil assembly further includes one or more transmitter coils and an assembly of one or more receiver coils. The one or more transmitter coils are arranged so as to be near the eye, and operably coupled to a transmitter driver. In particular embodiments, the transmitter coils are placed in proximity to the eye such that the coil(s) are in the near field of the transmitter coils. The one or more receiver coils also are placed near the scleral search coils and operably coupled to the receiver-amplifier circuitry.

The transmitter coils are pulsed to generate bursts of magnetic field energy, which stimulate the resonant coils in the scleral lens. After each burst of pulses, the one or more receiver coils act as directional antennae, transducing the electromagnetic field radiated by the resonating scleral coils. After amplification, these waveforms are digitized. As the magnitudes of the received waveforms depend on the position and orientation of the resonating coils on the eye relative to the set of receiver coils, by using this magnitude information, the position and orientation of the resonating coil/search coil assembly relative to the receiver coils are computed (horizontal, vertical, and torsional components). In further embodiments, the system includes three or more or six or more receiver coils that are disposed about the scleral search coil (s), the number of receiver coils be selected so as to be capable of detecting a desired number of degrees of freedom. For example, a scleral search coil on the eye can be used to detect up to five degrees of freedom and so five or more, more particularly six to eight receiver coils would be used in such cases so that five or six to eight signals are provided for determining the position and orientation of the search coil or search coil assembly.

The wireless coil system of the present invention will advantageously allow freedom of head movement, and measurement of eye movements in situations not currently possible with wired search coil systems. High head acceleration stimuli are of increasing importance in oculomotor research, and the compact, light weight system afforded by the present invention is much better able to deliver accurate data under these experimental conditions.

The wireless assembly including the coil and biocompatible material in which the coil is disposed will not be susceptible to wire breakage and should be more comfortable as compared to prior art devices. The scleral search coil or coil assembly of the present invention device will be particularly advantageous for animal studies as the elimination of the wire can greatly simplify surgical coil implantation procedures, decrease risk of infections, and eliminate the need for repeat surgeries to repair broken wires. It will also allow head-free recordings which are problematic with animals now due to the magnetic field pickup artifact of the metallic search coil connectors mounted on the animal's head.

Also featured are methods embodying such wireless scleral search coils and systems of the present invention.

The wireless scleral search coil assembly and systems and methods embodying same of the present invention should have a number of beneficial or advantageous affects. As indicated herein existing search coil systems are not mobile, employ various methods of head stabilization to keep the eye near the center of the magnetic field cube and are unable to track head translations. In contrast, the system and coil assembly of the present invention is easily adaptable to be portable. Such portability would encourage the use of bedside and clinical eye movement recordings as well as use in novel situations and locations. Head free experiments with search coils also would become simple as compared to prior art search coils.

The ability to carry out experiments with the head and body unrestrained has significant bearing on the development of strategies to induce and assess vestibular rehabilitation. Work on context-specificity (Shelhamer M, Clendaniel RA. Context-specific adaptation of saccade gain. *Exp Brain Res* 2002a; 146:441-450; Shelhamer M, Clendaniel R. Sensory, motor, and combined contexts for context-specific adaptation of saccade gain in humans. *Neurosci Lett* 2002b; 332:200-204; Shelhamer M, Clendaniel R, Roberts T, Patel V, Trillenberg P. Vestibular and oculomotor context cues for adapted responses. (Presented at the Vestibular Satellite Meeting of the 1999 Neural Control of Movement Meeting, Princeville, Hi.); Shelhamer M, Peng G C Y, Ramat S, Patel V. Context-specific adaptation of the oculomotor response to lateral translation using roll and pitch head tilts as contexts. *Exp Brain Res* 2002; 146:388-393; Shelhamer M, Robinson D A, Tan S. Context-specific adaptation of the gain of the vestibulo-ocular reflex in humans. *J Vestib Res,* 2:89-96) demonstrates that adaptive alterations (e.g., changes in VOR or saccade gain) that are induced in one context may not generalize fully to other contexts. Some of the contexts used in these experiments were eye and head position, and gravity level. The results suggest that rehabilitation procedures carried out in an artificial lab environment (for example with constrained head or body motion) might not generalize fully to activities under more normal circumstances.

The coil assembly, system and methods of the present invention would allow for substantial extension of the range of body motions allowed, to include jogging, running, bending over, kneeling down, as well as changes between laying, sitting, and standing, and reaching—typical activities that are problematic for vestibular patients (Cohen H S, Kimball K T. Development of the vestibular disorders activities of daily living scale. *Arch Otolaryngol Head Neck Surg* 2000; 126: 881-887). Even if eye movements are not actually measured in patients during rehabilitation procedures, the ability to measure eye movements during these behaviors in supporting laboratory studies would make possible the study of adaptive mechanisms in situations that are more similar to those in normal life outside the lab.

Another area of potential use of the coil assembly, systems and methods of the present invention is in parabolic flight experiments, which investigate adaptation to weightlessness. Presently, parabolic flight is a procedure in which an aircraft (i.e., a NASA KC-135) flies a series of parabolic arcs, providing alternating periods of 0 g and 1.8 g, approximately 25 sec each. It is a demanding environment for life sciences research, because it allows little time for recovery from equipment problems. Scleral coil disadvantages such as the tendency for breakage and discomfort become especially problematic in such an environment. Because of this, video and EOG systems have been used to measure eye movements in previous reported flight experiments (Shelhamer et al. 1999, Clendaniel et al. 1999). These experiments, which involve adaptation of saccades and the VOR, would definitely benefit from the use of wireless search coils, with their increased accuracy. In addition, such wireless search coils would allow for more free movement, making for example the measurement of VOR with rapid pitch motions more feasible. It should be noted that, despite the difficulties conventional search coils have been used in parabolic flight (Cheung B S, Money K E, Howard I P. Dynamics of torsional optokinetic nystagmus under altered gravitoinertial forces. *Exp Brain Res* 1995; 102:511-518; Cheung B S, Money K E, Howard I P. Human gaze instability during brief exposure to reduced gravity. *J Vestib Res* 1994; 4:17-27). Because of its portability, the coil assembly and related systems of the present invention can be easily adapted for use in parabolic flight experiments as compared to conventional search coil systems.

Dynamic posturography is a procedure in which standing posture is perturbed by various combinations of ankle tilt and visual motion, and the resulting head and body motions measured to assess the ability to control upright stance. Only relatively recently have eye movements been measured during these procedures, in order to assess gaze control during the perturbations. For example, Crane & Demer (Crane B T, Demer J L. Gaze stabilization during dynamic posturography in normal and vestibulopathic humans. *Exp Brain Res* 1998; 122:235-246) used search coils during such experiments. Their system had a calibration that was constant to within ±5% as long as the eyes remained within a 58 cm cube. While this allows a range of head motion, the head nevertheless must be somewhat restricted. A typical search coil system might have an error due to head translations (in the non-uniform magnetic field) of approximately 0.03°/cm within a 30 cm cube (Grossman G E, Leigh R J. Instability of gaze during locomotion in patients with deficient vestibular function. *Ann Neurol* 1990; 27:528-532). Even with this performance, there is almost 1° of error at the ends of the range, and so head/body motion must be somewhat restricted. Because of its portability, the coil assembly and related systems of the present invention can be easily adapted for use in such dynamic procedures as compared to conventional search coil systems as well as not being limited by the constraints imposed by the cubic array of magnets used with conventional search coils The measurement of gaze stabilization while walking is another important line of investigation, which is indicative of the trend toward assessing vestibular and oculomotor function in as natural circumstances as possible. This is currently done on treadmills and moving platforms (e.g., Mulavara A P, Verstraete M C, Bloomberg J J. Modulation of head movement control in humans during treadmill walking. *Gait Posture* 2002; 16:271-282; Imai T, Moore S T, Raphan T, Cohen B. Posture and gaze during circular locomotion. *Ann NY Acad Sci* 2001; 942:470-471; Moore S T, Hirasaki E, Raphan T, Cohen B. The human vestibulo-ocular reflex during linear locomotion. *Ann NY Acad Sci* 2001; 942:139-147), typically with video eye-tracking systems, with their attendant problems as noted previously. Although search coils have been used in such an experiment (Grossman G E, Leigh R J, Bruce E N, Huebner W P, Lanska D J. Performance of the human vestibuloocular reflex during locomotion. *J Neurophysiol* 1989; 62:264-272; Grossman G E, Leigh R J. Instability of gaze during locomotion in patients with deficient vestibular function. *Ann Neurol* 1990; 27:528-532), the subjects' movements were still restricted (see above); presently such procedures must take place on a treadmill or other apparatus where the subject is kept in close proximity to the eye-movement instrumentation. Because of its portability, the coil assembly and related systems of the present invention can be easily adapted for use in measurement of gaze stabilization while walking as compared to conventional search coil systems as well as not being limited by the constraints imposed by the cubic array of magnets used with conventional search coils Also, the wireless scleral search coil assembly of the present invention can be more easily configured to increase the comfort level of the subject in particular when compared to the present coil assemblies in which a wire extends from the lens to the instrumentation. Increasing comfort thereby beneficially decreases distraction of the subject caused by discomfort and thus tends to increase the quality of data, while extending the duration of experiments. A more comfortable coil assembly also should beneficially reduce dependence on topical anesthesia to deal with possible discomfort when using conventional eye coils. Because the anesthetic often affects visual acuity, this would have positive implications for experiments where acuity is an important factor.

The wireless search coil assembly and systems of the present invention also would have beneficial advantages in regards to animal studies. As to animal studies the wireless search coil of the present invention would simplify surgical procedures and this along with the portability and size of the related systems would also simplify the experimental setup.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 2A:
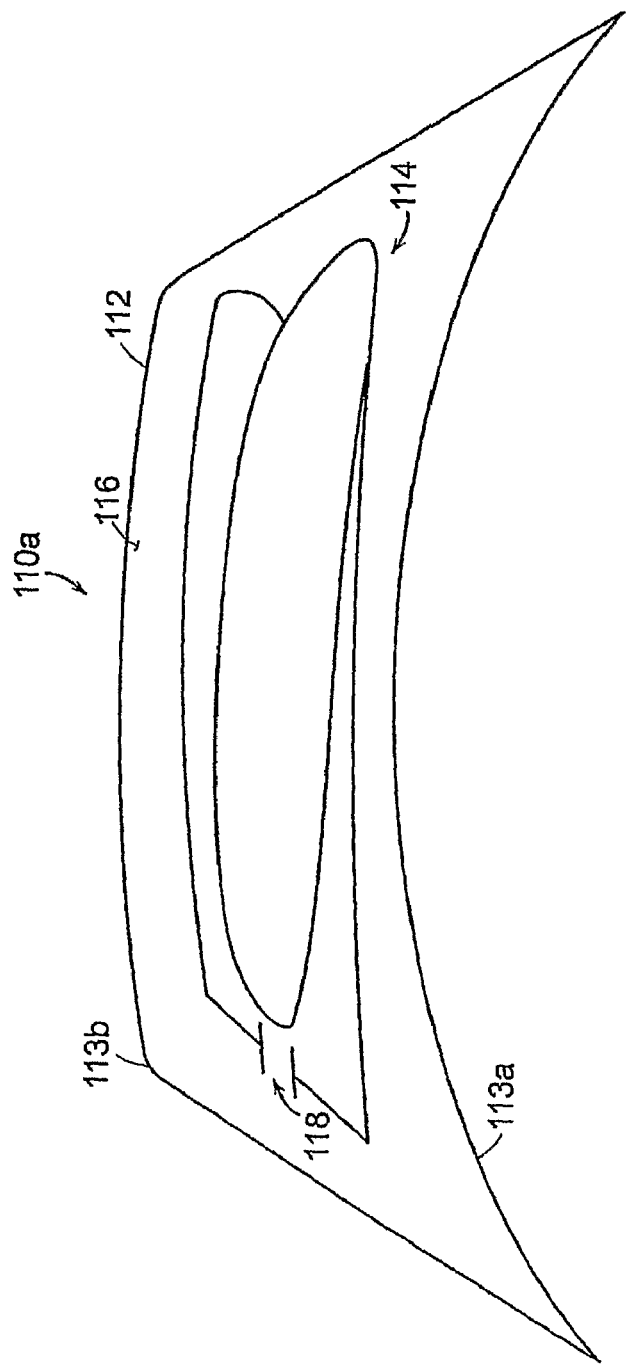
FIGS. 2A,B are an illustrative view and a schematic view respectively that show two arrangements of a scleral search coil assembly according to the present invention with a single coil (FIG. 2A) and with more two coils (FIG. 2B)
Figure 2B:
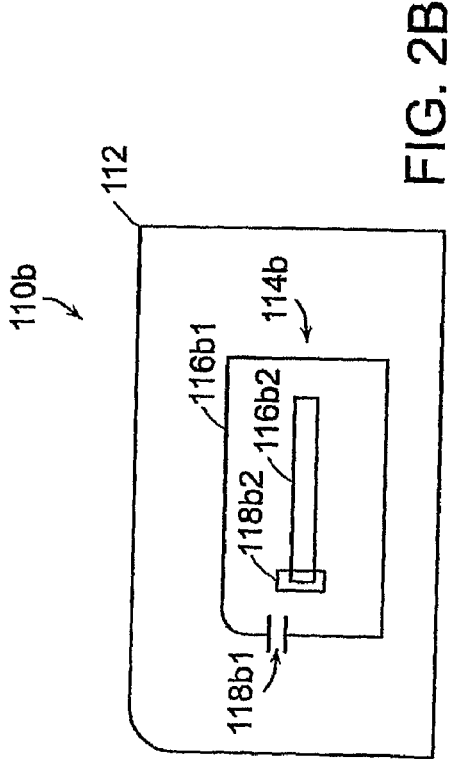

Referring now to the various figures of the drawing wherein like reference characters refer to like parts, there is shown in FIGS. 2A,B two embodiments according to the present invention of a scleral search coil assembly 110a,b, where FIG. 2A is an illustrative view of one embodiment and FIG. 2B is a schematic view of the other embodiment. In the following reference numeral 110 is used when referring to the scleral search coil assembly in general such as in the discussion concerning FIG. 3A. The scleral search coil assembly 110a illustrated in FIG. 2A includes a support member 112 and a resonating coil 114a that is disposed within the support member. The resonating coil 114a is arranged so that its plane is perpendicular to the line of sight. With such a coil arrangement, when the search coil assembly 110a is on the eye it should be possible to deduce the direction of gaze (horizontal and vertical position) with the appropriate number and placement of receiver coils as hereinafter described.

The support member 110 is made of any of a number of biocompatible materials known in the art and appropriate for the intended use of being removably disposed on the eye of a human or animal. In further embodiments and as is known to those skilled in the art, the support member has a thickness and shape that also is selected so as to be compatible with the surface contour of the eye. In an exemplary illustrative embodiment, a bottom surface 113a of the support member 112 would be formed so as to present a generally concave shape and a top surface 113b thereof would be formed so as to have a generally concave shape much like the shape of a conventional concave lens. The support member also is preferably made of a flexible material and whose thickness is set so as to minimize the possible irritation and/or discomfort to the subject or patient when the search coil assembly 110a is disposed on the eye(s) of the subject. In particular embodiments, the support member is made form a flexible bio-compatible polymer.

As is known to those skilled in the art, in animal studies the resonating coil is typically directly secured to the eye using any of a number of techniques known to those skilled in the art (e.g., coil is sutured to eye). As such, a search coil assembly of the present invention can include a resonating coil 114 without the support member.

In exemplary embodiments, the resonating coil 114 includes a multiple turn loop 116 of wire (e.g., fine wire) and a capacitor 118 that are arranged so as to be in series so as to form a coil-capacitor circuit. As is known to those skilled in the art, the capacitor and the inductance of the wire loop 116 can be set so that the circuit that is created by the combination will resonate at a given frequency. In the case of the present invention, electromagnetic pulses are provided to stimulate the resonating coil 114. The resonating coil 114 also is configured so that after the pulses are stopped, the resonating coil continues to oscillate with a dampened sinusoid which is radiated from the resonating coil.

When the transmitted pulses stop, the eye coil continues to oscillate for several cycles. The amplitude and duration of the oscillations depend on the specific characteristics of the resonant circuit, most notably the "quality factor" or Q, which in turn depends on the physical properties of the circuit elements such as resistance of the wire of the resonant coil. As described further herein, these continuing oscillations are radiated from the eye coil and captured by a separate receiver coil.

The wire loop 116 including the number of turns and the diameter and the capacitor are each such as to cause the resonating coil 114 to oscillate at a desired frequency. Also, while a wire loop 116 having a general circular shape is illustrated this shall not be construed as a limitation as the wire loop can be arranged so as to form any of a number of shapes known to those skilled in the art including but not limited to rectilinear (e.g., square). In the case where such a scleral search coil 110a is disposed in both eyes of the subject, it also is contemplated that the wire loop 116 including the number of turns and the diameter and the capacitor for each resonating coil 114 are such as to cause the resonating coil in one eye to oscillate at a different frequency from the resonating coil in the other eye.

Referring now to FIG. 2B there is shown a schematic view of another embodiment of a scleral search coil assembly 110b that includes a support member 112 and two resonating coils 114b1,b2 that are disposed within the support member. In the illustrated embodiment the first and second resonating coils 114b1, b2 are arranged so that the plane of the first resonating coil is perpendicular to the line of sight and so the pane of the second resonating coil 114b2 is approximately perpendicular to the plane of the first resonating coil. With the second resonating coil 114b2, it should be possible to deduce the direction of gaze (horizontal and vertical position) and the torsional rotation about the line of sight with the appropriate number and placement of receiver coils as hereinafter described.

In further embodiments, the capacitor 118 is a miniature capacitor (e.g., surface mount device) that is in series with the wire loop 116 and embedded or implanted in the support member 112. In alternative embodiments, the resonant coil 114 is configured so as to be self-resonating (i.e., without a capacitor). In yet further embodiments, the wire loop 116 and capacitor 118 are fabricated as an integral assembly by way of, for example, a flexible circuit that is deposited on the support member 112. The foregoing embodiments are exemplary and illustrative and thus, the coil assembly of the preset invention also shall include other arrangements and configurations that are adaptable based on the teachings of the preset invention to achieve a wireless effect as described herein.

Figure 3A:
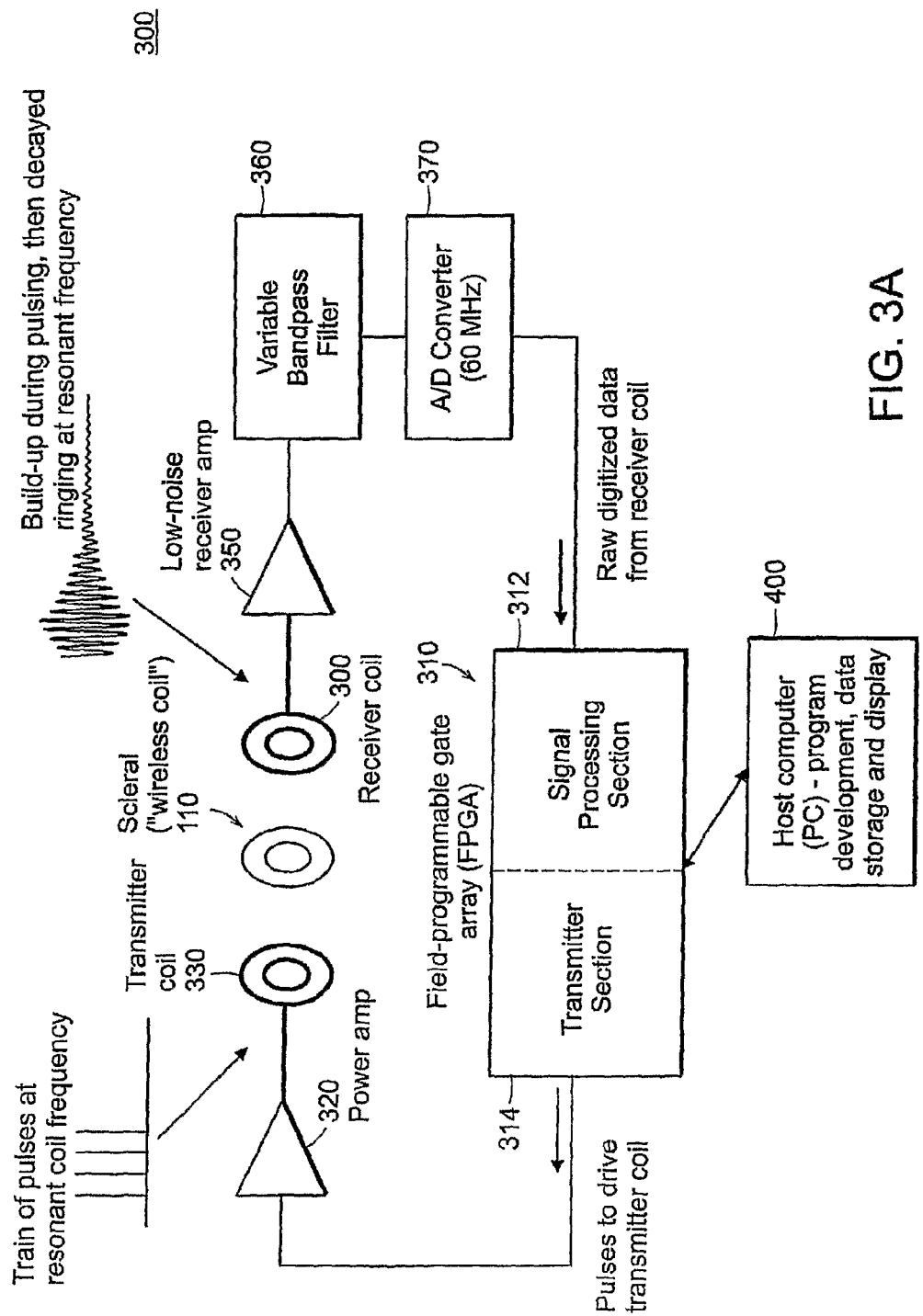
FIG. 3A is a block diagram of a wireless coil system according to the present invention.
Figure 3B:
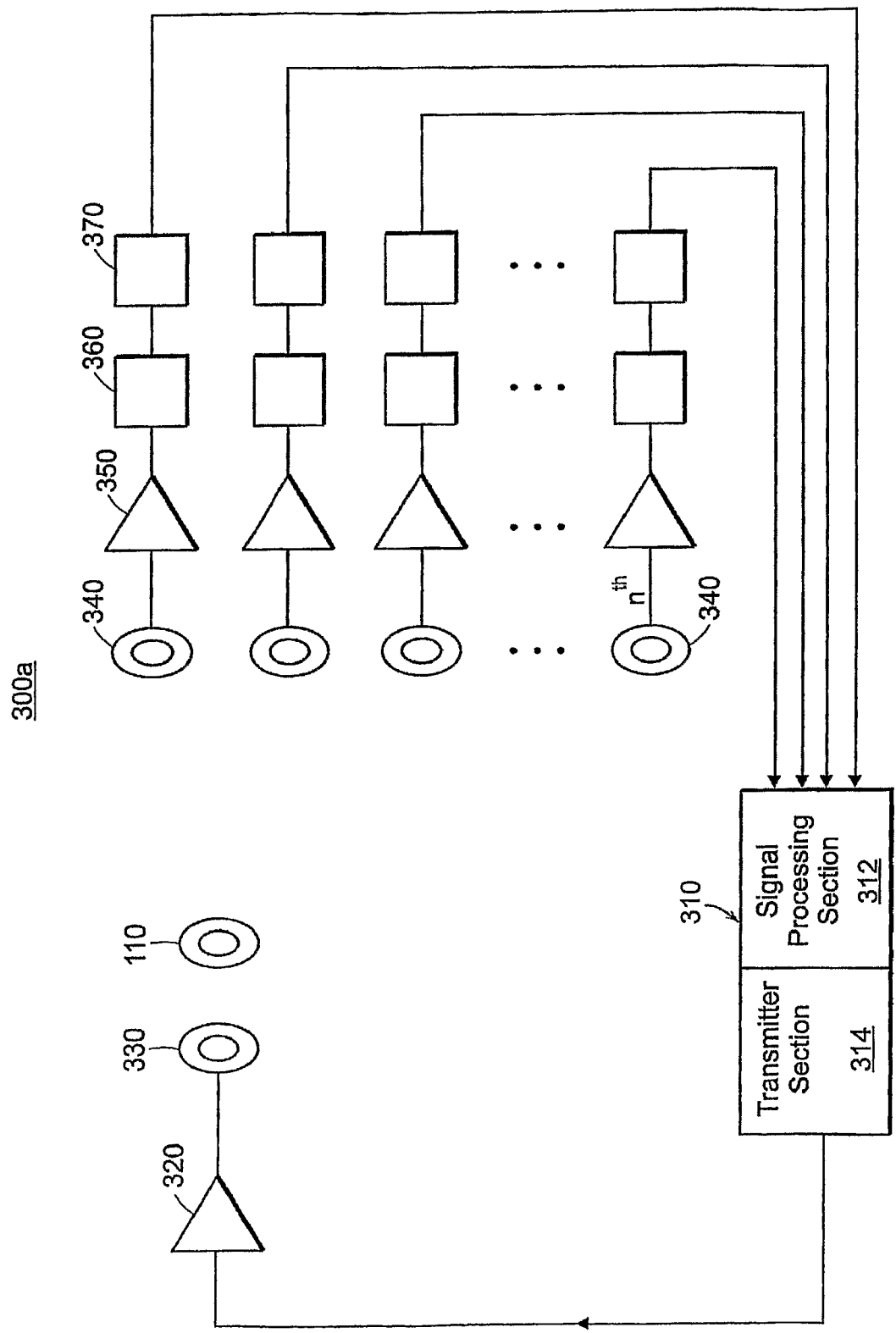
FIG. 3B is a block diagram of a wireless coil system according to the present invention embodying N receiver coils.

Referring now to FIG. 3A, there is shown a block diagram view of a wireless search coil system 300 according to the present invention, which system includes one or more wireless scleral search coils 110 that is disposed on one or both eyes of the subject. A block diagram view of a wireless search coil system 300a according to the present invention including N receiver coils is shown in FIG. 3B. It should be recognized that the wireless scleral search coil can be either of the first or second embodiments described herein in connection with FIGS. 2A,B as well as any other such search coil assembly embodying the methodology and teachings provided herein.

In its broadest aspects, such a wireless search coil system 300 includes a transmission sub-system, a signal reception sub-system and a calculation sub-system. The transmission sub-system generates and transmits electromagnetic pulses or bursts of magnetic field energy, which stimulate the one or more resonating coils 114 in the scleral coil assembly 110 so as to resonate the resonating coil at the desired frequency. After the transmission signals are stopped, the one or more resonating coils 114 (FIG. 2A) of the coil assembly 110 continues to oscillate and outputs signals therefrom, which signals are received by the reception sub-system (e.g., the reception antennas or coils thereof). The reception sub-system receives the signals from the coil assembly 110 and appropriately processes the signals (e.g., filtering) so the signals can be further processed in the calculating sub-system. The calculating sub-system, using the received signals from each of the receiving coils, determines the position (e.g., horizontal, vertical) and torsional rotation of the coil assembly and thus, measures or determines the movement of the eye to which the search coil assembly 110 is on.

As indicated above, the transmission sub-system generates and transmits electromagnetic pulses or bursts of magnetic field energy to stimulate the one or more resonating coils 114 in the scleral coil assembly 110 so as to resonate the resonating coil at the desired frequency. Thus, in one exemplary embodiment, the transmission sub-system is configurable to generate and transmit electromagnetic pulses (i.e., sequence or train of such pulses) to stimulate one resonating coil at a time (i.e., in seriatim stimulation of the resonating coils). In another exemplary embodiment, the transmission sub-system is configurable to generate and transmit electromagnetic pulses of different frequencies to stimulate all of the resonating coils of a given search coil assembly 110 at the same time. In the case of this another embodiment, the reception sub-system are configurable so as to parse out or separate the received signals corresponding the respective resonating coil.

As is known to those skilled in the art, the magnitudes of the received signals depend upon the position and orientation of the one or more resonant coils 114 on the eye relative to the receiver coil(s) (e.g., set of receiver coils) of the reception sub-system. By using this magnitude information, the position and orientation of the coil assembly 110 with respect to the receiver coil(s) can thus be computed (e.g., horizontal, vertical and torsional components and translational components).

Such a wireless search coil system 300 of the present invention is particularly advantageous as compared to conventional or commercially-available systems in that the system of the present invention easily allows for freedom of head movement, and measurement of eye movements in situations not currently possible with wired search coil systems. High head acceleration stimuli are of increasing importance in oculomotor research, and the system of the present invention because it can be made compact, portable and of light weight as compared to conventional systems, can deliver accurate data under these experimental conditions. The wireless coil assembly of the present invention will not be susceptible to wire breakage as readily occurs with conventional eye coils. Further, because such a wireless coil assembly does not involve the use of an interconnecting wire(s), surgical coil implantation procedures used in animal studies can be greatly simplified and thus also decrease risk of infections and eliminate the need for repeat surgeries to repair broken wires. Such coil assemblies and systems of the present invention also allow head-free recordings which are problematic with animals now due to the magnetic field pickup artifact of the metallic search coil connectors mounted on the animal's head.

Also, a wireless search coil system of the present invention is advantageous as compared to conventional systems as the system of the present invention can detect and measure translational movement between the search coil assembly and the receiver coil(s). In this regard translational movement or motion is relative movement between the search coil assembly and the receiver coil(s) that is not accompanied by movement of the eye. For example, such relative movement could result from movement of the search coil on the eye or a displacement of the receiver coil(s). The search coil system of the present invention can distinguish between signals representative of translation movement and signals representative of rotational movement of the eye, based on the pattern of signals being received. In this way, the search coil system of the present invention can detect and measure such translation movement and thereafter adjust future computations to compensate for prior translational movement. Further, because such a search coil system can compensate for the translational movement, the receiver coils do not have to be rigidly coupled to the subject.

In illustrative embodiments, such a wireless search coil system 300 includes a field-programmable gate array 310, a power amplifier 320 operably coupled to one or more transmitter coils 330, a low-noise receiver amplifier 350 operably coupled to one or more receiver coils 340, a variable bandpass filter 360, and an analog to digital converter 370. Such a wireless search coil system is further selectively and operably coupled to a host computer 400. While the host computer 400 is depicted as being operably coupled to the field programmable gate array 310, the search coil system 300 does not have to be coupled to the host computer at all times for the system to operate as described herein, including when the search coil system is acquiring and processing data. In exemplary embodiments, the host computer 400 is coupled to the field programmable gate array 31 when downloading programming instructions and criteria to the gate array or when downloading data and computational results from the gate array following data processing within the gate array.

In further embodiments, the functionalities or components of the search coil system 300 are selected and arranged so that the search coil system is portable and capable of being localized or carried by the subject. In yet further embodiments, the functionalities or components of the search coil system 300 are distributed about the subject. For example, the transmitter and receiver coils 330,340 are located in proximity to the search coil assembly 110 and the other functionalities or components of the system are disposed at another location on the subject (e.g., located in a housing secured to the belt of the subject).

While portability is desired for such a search coil system 300 of the present invention, it is contemplated and thus is within the scope of the present invention for portions of the system to be located on the subject and for other portions to be located remote from the subject. For example, the amplifiers 320, 350 and other functionalities (310, 360, 370) of the system are located remote from the subject (e.g., on the treadmill structure) and the transmitter coils 330 and receiver coils 340 are located on the subject proximal to the eyes and with the wireless search coil assembly 100 on each eye. In such a case, the transmitter and receiver coils 330, 340 would be interconnected to the amplifiers by interconnecting wires or a wireless (e.g., IR) communication network. The functions and operations of the system are more fully described below in connection with FIGS. 4A,B.

The host computer is any of a number of well known computer systems including a microprocessor, memory, storage device(s), input device(s), display device (e.g., CRT or LCD) and one or more software programs for execution on the microprocessor. Such software programs also include the programs used to develop the programs downloaded onto the field programmable array 310 as well as displaying data or results of the performance of an eye measurement, outputting results to a printing device as well as storage of such data on the storage devices. Such a host computer 400 also can be operably coupled to a network and thus such data and results also can be provided or made available over such a network to others, including the storage of such data in storage devices operably coupled to the network and accessible to others connected to the network.

The field programmable gate array (FPGA) 310 is any of a number of devices known to those skilled in the art, which are capable of being programmed to perform specified functions and operations according to an applications program downloaded from the host computer 400 and so that substantial processing is preferably carried out in real time. While a field programmable array 310 is described, the present invention is not to be construed as being limited to such a device as any of a number of other devices known to those skilled in the art (e.g. a digital signal processor (DSP) or microprocessor) can be adapted for such use. As is known to those skilled in the art, the created program is downloaded into the field programmable gate array 310 so that the gate arrays are configured so the FPGA is capable of executing the functions to be carried out by the program. In other words, the FPGA is hard wired so as to carry out the functions instead of being carried out as part of the execution of an applications or software program. As indicated above, it is contemplated that such functions be carried out using software being executed in a DSP or microprocessor, or in a different or the same FPGA.

The downloaded program in the FPGA 310 is such as to control the transmission, signal reception, signal processing and calculating functions of the system as more particularly described below in connection with FIGS. 4A,B. The downloaded program in the FPGA 310 would be such as to form a transmitter section 314 that generates a sequence of pulses at the resonant frequency of the resonate coil 114 (e.g., 3-6 MHz). When the wireless search coil assembly 100 includes two or more resonating coils, the downloaded program in the FPGA 310 would cause the transmitter section 314 to generates a sequence of pulses at a first frequency to stimulate one resonating coil 114$b$1 (FIG. 2B) and to generates a sequence of pulses at a second frequency to stimulate the second resonating coil 114$b$1 (FIG. 2B), where the first and second frequencies are different from each other.

As indicated herein, the transmitting sub-system of a search coil system of the present invention is configurable so that the sequence or train of electromagnetic pulses are generated or transmitted in seriatim or at the same time. Thus, in further embodiment, the downloaded program in the FPGA 310 would cause the transmitter section to generate the sequence of pulses at the first and second frequencies such that they are transmitted in seriatim or at the same time.

Such pulses would be outputted to and drive the power amplifier 320 that is operably and electrically connected to the FPGA 310. The power amplifier 320 is operably and electrically connected to the transmitter coil(s) 330, and the amplifier drives the transmitter coil(s). The power amplifier 320 is any of a number of devices or amplifiers know to those skilled in the art and that is appropriate for the intended use. In further embodiments, the power amplifier 320 is of the type and size whereby the power amplifier could be removably disposed on the subject while performing the eye measurement process.

While one transmitter coil 330 is shown, it should be recognized that the search coil system of the present invention is configurable to include more than one transmitter coil. For example, it is contemplated that the search coil system of the present invention would be used to measure eye movement for both eyes of the subject. Thus, the system is configurable so as to include one transmitter coil 330 for each eye. In further embodiments, the search coil system is configurable so as to provide a power amplifier 320 for each transmitter coil.

The transmitter coil(s) 330 is located in close proximity to the wireless scleral coil assembly 110 on the eye (e.g., 2-5 cm from the eye) so that the coil assembly would be considered as being in the near field of the transmitter coil. In particular embodiments, the transmitter coil(s) 330 is located on a support member (e.g., a biteboard or spectacle frames) so that the transmitter coil is maintained in fixed relation to the wireless search coil 110 during the eye measurement process. In the case where there is a transmitter coil 330 for each eye, the transmitter coils 330 are located on a support member so that each transmitter coil is maintained in fixed relation to the wireless search coil 110 for the corresponding eye during the eye measurement process.

Also, it is well within the skill of those knowledgeable in the arts to provide a transmitter coil 330 having a shape/configuration, size and makeup (e.g., material) that is capable of transmitting the signal(s) in the frequency range(s) in which the signal pulses' would lie as well as directing the signals towards the coil assembly 110.

The downloaded program in the FPGA 310 also is such as to form a signal processing section 312 (e.g., a synchronous demodulator section) that processes raw digitized data so as to determine and provide an indication or measurement of the position and orientation of the eye. As also indicated herein, the signal processing section 312 can process the raw digitized data so as to detect and determine translational movement between the search coil assembly and the receiver coil (s). More particularly, the digitized data stream is supplied to the FPGA 310 wherein it is processed to yield an estimate of the instantaneous orientation of the resonant coil 114 with respect to the transmitted and receiver coils 330, 340. Such processing functions of the FPGA 310 are discussed in further detail hereinafter. The raw digitized data being provided to the FPGA 310 is obtained as follows via the receiver coil 3340, the receiver amplifier 350, the filter 360 and the A/D converter 370.

As described herein, the transmission sub-system of the search coil system 300 is operated so that the sequence of pulses stimulating a resonating coil 114 of a given search coil assembly 110 are stopped and thereafter the resonating coil 114 outputs or re-radiates signals therefrom (e.g., a decaying sinusoid). In this regard, after a predetermined period of time has elapsed since the stoppage of signals from a prior generation cycle, the FPGA 310 would cause another sequence of pulses to be generated. The predetermined period of time is set so as to allow sufficient time for the signal reception and calculating sub-systems to carry out their respective functions and operations.

These signals being outputted by the resonating coil 114 are detected by the receiver coil 340. The receiver coil 340 is located in proximity to the wireless scleral coil assembly 110 on the eye (e.g., 5-20 cm from the eye). In particular embodiments, the receiver coil 330 is located on a support member (e.g., a biteboard or headband) so that the receiver coil(s) is maintained in fixed relation to the wireless search coil 110 during the eye measurement process. Thus, the transmitter coil 330 and the receiver coil 340 are both maintained in fixed relation to the wireless search coil 110 during the eye measurement process.

The signals from receiver coil 340 are inputted to a receiver amplifier 350 that is operably and electrically coupled to the receiver coil. In particular embodiments, the amplifier is characterized as being of low-noise and wide bandwidth. Such an amplifier is any of a number of amplifiers known to those skilled in the art that has such characteristics (e.g., an instrumentation amplifier) and which is appropriate for the intended use. In further embodiments, the receiver amplifier 350 is of the type and size whereby the amplifier can be removably disposed on the subject while performing the eye measurement process.

The amplified signals from the receiver amplifier are input to the bandpass filter 360. The bandpass filter filters the amplified signals so the signals having a frequency that is not within a predetermined bandwidth are essentially blocked. In other words, the strength of the other signals is at or below a threshold level such that these other signals will not significantly impact or affect the further processing and calculating functions. Although the bandpass filter 360 is depicted as being after the receiver amplifier, it is within the skill of those in the art to reconfigure the circuitry so such filtering occurs before amplification.

The filtered analog signals are outputted to an A/D converter 370 which digitizes the signals (e.g., at 60 Hz) and outputs the digitized signal to the FPGA 310, more particularly the signal processing section 312 thereof. The A/D converter 370 is any of a number of such analog to digital converters known to those skilled in the art and appropriate for the intended use. It should be noted that it is within the scope of the present invention to utilize a device that combines any of the above described functionalities that is adaptable for use in the system of the present invention.

Although a single receiver coil 340 is illustrated in FIG. 3A, this is not a limitation. As shown in FIG. 3B, a search coil system 300*a* of the present invention also is configurable so as to include N receiver coils, where N is an integer that is ≧2, more particularly ≧3, more particularly ≧6 or more particularly ≧8. In more particular embodiments, the number of receiver coils is generally established so as to create an array of receiver coils that provides the number of output signals necessary to determine the orientation and/or position of the search coil. A single circular eye coil has five spatial degrees of freedom—three location and two rotation (rotation about the axis of the coil is not detectable). Therefore, at least five independent signals are needed in order to determine the orientation and position of a single eye coil. If one is interested in obtaining only location information (e.g., horizontal and vertical components), such information can be obtained using a lesser number of independent signals (e.g., at least three signals).

A single set of three orthogonal receiver coils returns only three signals, which is not enough information to determine the orientation and position of the eye coil, unless some of the coordinates are known and fixed. However, such a set would be generally sufficient to obtain location information. In order to determine the wireless coil position and orientation (i.e., all five degrees of freedom), six to eight coils are necessary, which are sufficient to determine all five wireless coil position and orientation parameters.

Thus, in further embodiments, a search coil system of the present invention is configured with one or more sets of three or more receiver coils 340 that are oriented so as the receivers coils are approximately orthogonal to each other. Each of the receiver coils 340 also is mounted to a support member or frame so that the receiver coils are maintained in fixed relation to the eye and also so that each are maintained in fixed relation to the transmitter coil(s) 330. As described further herein, the receiver coils are so mounted so that a unique solution to the translation/orientation determination can be made, via non-linear optimization routines embedded in the program embodied in the FPGA 310.

Figure 1:
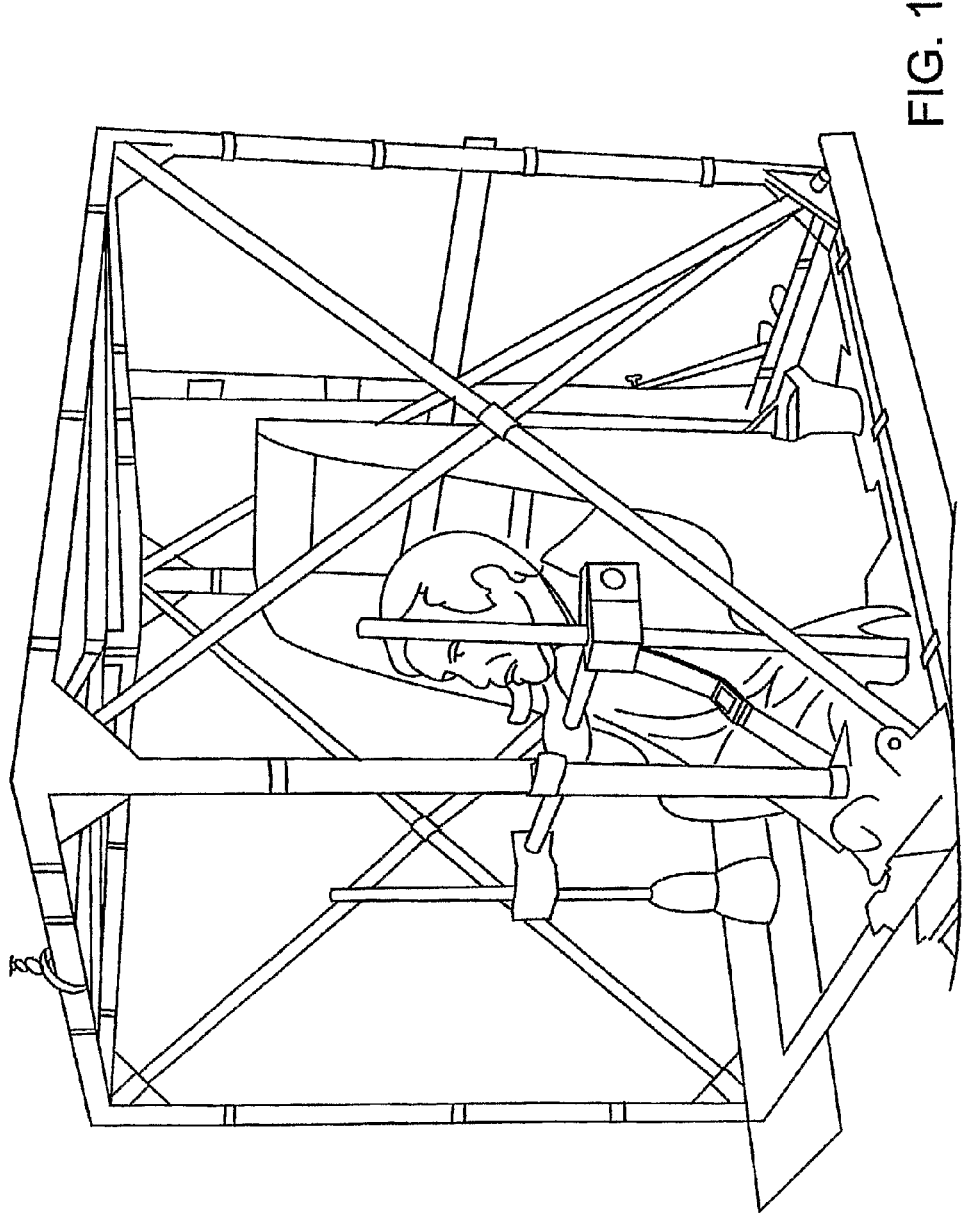
FIG. 1 is an illustration of a conventional system in which the subject is in a chair.
Figure 4A:
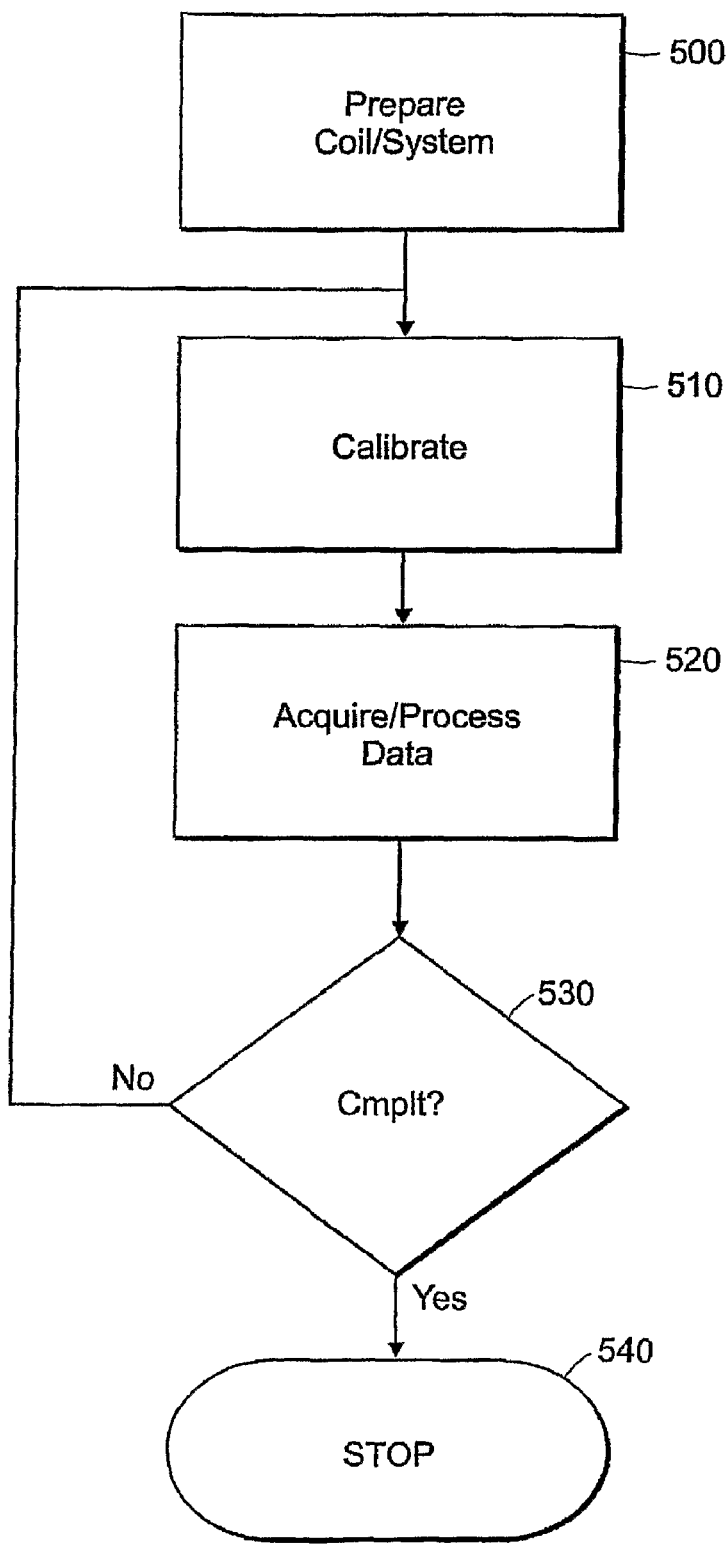
FIG. 4A is high flow diagram of the overall process for eye measurement accruing to the present invention.
Figure 4B:
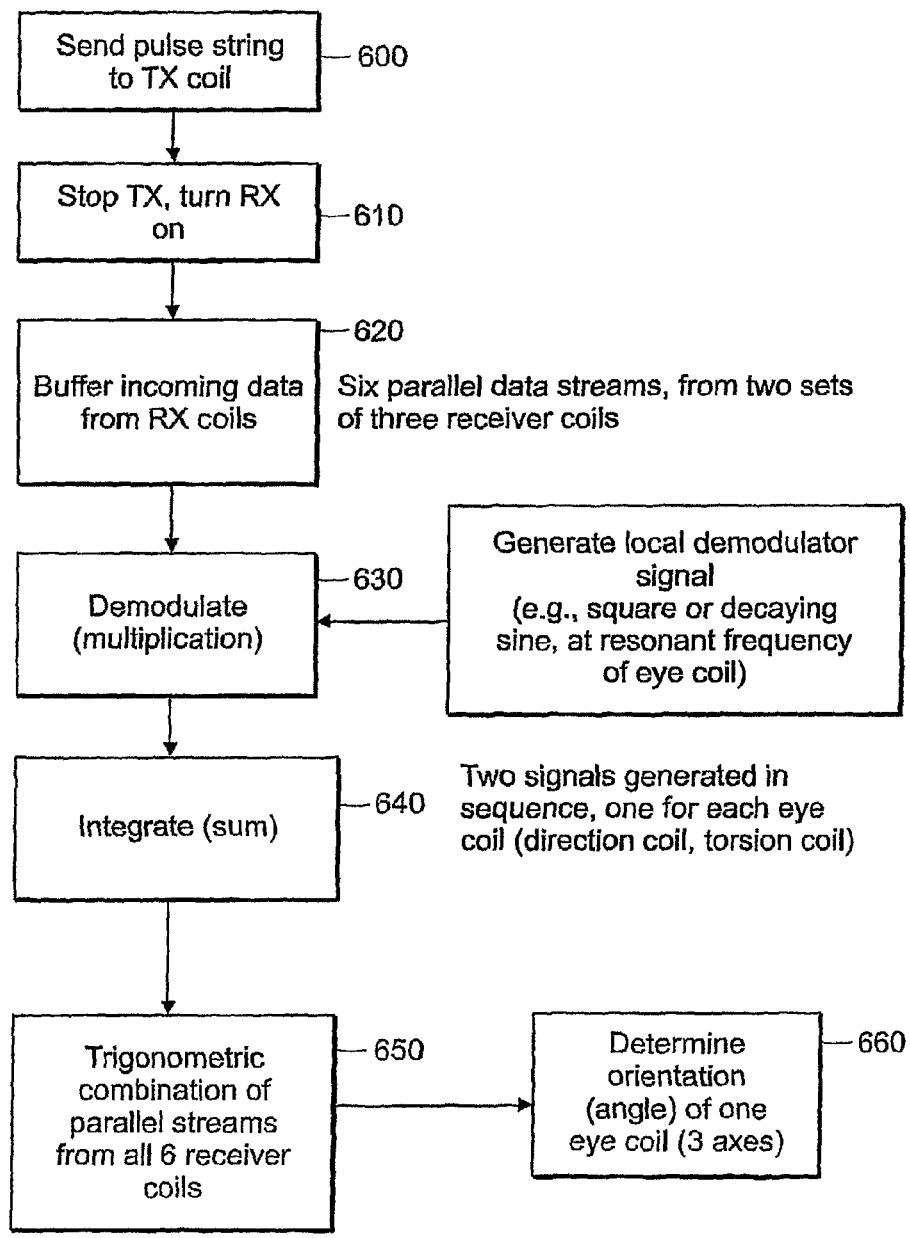
FIG. 4B is high flow diagram of the data acquisition and processing methodology of the present invention.

Referring now to FIGS. 4A,B there is shown a high flow diagram of the overall process of eye measurement (FIG. 4A) and a high level flow diagram of the data acquisition and processing methodology of the present invention (FIG. 4B). Reference shall be made to FIGS. 1-3 as well as the related discussion for components or functionalities of the search coil system 300, 300*a* and the wireless search coil assembly 110 not otherwise provided below. Further, one skilled in the art based on the foregoing descriptions, the flow diagrams and the following discussion can prepare an applications program or the program to be downloaded to the FPGA 310 so as to carry out the herein described signal generating and data processing functions.

After preparing the subject for the eye measurement procedure as well as for any other procedure or task that is being performed concurrently with the acquisition of the eye measurement data (e.g., walking by the subject) the search coil system 300, 300*a* including the wireless scleral search coil assembly 110 are prepared for use, STEP 500. Such preparing includes locating the wireless search coil assembly 110 on one or both of the eyes of the subject and to take other steps appropriate for the procedure relating to the eyes, such as for example placing a patch over one of the eyes.

Such preparing also providing the other functionalities of the search coil system 300, so that they are localized to the subject. For example, the functionalities are mounted on a biteboard and the biteboard is given to the subject. Also, for example, some of the functionalities (e.g., transmitter coils are mounted to a framework that is secured to the head and the other functionalities are mounted to a biteboard. Such mechanisms or support members for holding the functionalities or system components are such that the transmitter and receiver coils are maintained in approximately fixed relation with respect to the head during the eye measurement process.

After preparing the subject and system for data acquisition, the search coil system is calibrated, STEP 510. Such calibration includes finding or determining the resonant frequency of each resonating coil 114 of the search coil assembly 110. This is readily accomplished using any of a number of techniques know to those skilled in the art, including use of an on-line frequency-estimation algorithm.

Other factors to consider in acquiring data is the relative positions and angles of the transmitter and receiver coils, and the exact orientation of the coil on the eye. The overall effects of these factors can be condensed into a single "sensitivity vector" for a given search coil assembly and a given direction of eye movement to be measured. This sensitivity vector is found by having the subject make a range of eye movements while signal levels are monitored. An in vivo calibration process to determine this sensitivity vector is preferred to minimize the affect that these various parameters might change when the eye coil and system functionalities are attached to the subject.

After calibration is completed, signal data is periodically and continuously acquired from each resonating coil 114 of each wireless coil assembly 110 and such signal data is processed so outputs or indications of the orientation of the eye is provided to the clinician or user, STEP 520. Such information is acquired even though the subject is performing other tasks such as walking, experiencing weightless or elevated gravity, or any of a number of tasks as herein described where eye measurement information is a desired parameter to be considered. The acquisition and processing of the data is described more fully below in connection with FIG. 4B.

The search coil system of the present invention continues to acquire signal data from each resonating coil for each search coil assembly of the system (NO, STEP 530) until it is determined that the eye measurement process to be performed is completed. In the case where, the particular eye measurement technique being performed requires a re-adjustment or reconfiguration (e.g., moving the eye patch to another eye), the process is temporarily stopped until the re-adjustment or reconfiguration is accomplished and the acquisition of data is continued. When the process is completed (YES, STEP 530) the data acquisition process is stopped. Such stopping includes removal of the search coil assembly 110 from each eye and removal of the system functionalities.

As noted above the signal acquisition and data processing of the search coil system 300, is more particularly described in connection with FIG. 4B, which discussion follows. After the search coil system is otherwise prepared for signal acquisition and data processing (FIG. 4A, STEPS 500, 510), the controller of the search coil system namely the FPGA 310 proceeds to controls the overall operation of the system and thus the acquisition of the data for determining the orientation of the eye or each eye. The following discussion describes the process of determining the orientation of an eye when the system includes two sets of three receiver coils 340 (i.e., six receiver coils in total), a transmitter coil 330 and one resonating coil. However, it should be recognized that the below described procedure is repeated again for a second resonating coil at a different frequency. Also if the system is acquiring data for both eyes, the data acquisition processes is repeated for the second eye as well.

For example, if the resonating coil resonates at 2 MHz, a train of 10 transmitter pulses can be generated and transmitted in about 4.5 μs $[9\times(2\times10^6)^{-1}]$. If the resonating coil 114 is allowed to oscillate about 100 cycles to decay completely, this requires about 50 μs $[100\times(2\times10^6)^{-1}]$. Thus, the total time needed to stimulate the resonating coil 114 and then let its oscillations decay is on the order of 55 μs. Even if one allows for as much as 100 μs, this process produces estimates of eye position at a rate of 10 KHz. This would exceeds even the best of the available search coil systems, which have bandwidths of approximately 1 KHz, which is in fact sufficient to capture the dynamics of even the most rapid saccadic eye movements. This rapid sampling is possible due to the fact that, relative to eye movement bandwidth, the oscillations of the eye coil are extremely rapid.

As described above, the FPA 310 causes a sequence of pulses to be generated which ultimately drives the transmitter coil 330 for a given eye to stimulate a resonating coil 114 disposed in/on the search coil assembly 110, STEP 600. In addition to generating the signal pulses the FPGA 310 would typically also control the receiver sub-system so that its signal receiving capability is turned off when signal pulses are being transmitted from the transmitter coil 330 and turned on when such signals are not being transmitted. This on/off switching process is accomplished using any of a number of techniques known to those skilled in the art, such as for example, locating a switch between the receiver coil 340 and the amplifier 350 that opens or closes to isolate or connect the amplifier to the receiver coil(s). In this regard, it should be noted that such turning on/off of the signal receiving capability does not necessarily mean that the receiving amplifier 350 for example would be turned on and off.

After a sequence or train of pulses at the resonant frequency is transmitted, the transmission of such signals is stopped for a predetermined period of time, and the receiver sub-system is turned on, STEP 610. In a particular embodiment, the FPGA 310 is controlled to stop generating further signal pulses as the mechanism for termination of signal transmission. As indicated herein, after the predetermined period of time has elapsed, the FPGA would turn the receiver sub-system off and generate the next sequence or train of pulses.

As described herein following termination of signal transmission from the transmitter coil 330, the receiver coils 340 receive the signals radiating from a given resonating coil 114. As the search coil system includes two sets of three receiver coils mounted and arranged in a particular fashion, a stream of signals will be received by each of the receiver coils for processing through the amplifier 350, the bandpass filter 360 and the A/D converter 370. Consequently, six parallel digitized data streams will be generated from the six receiver coils. Thus, the FPGA 310 will buffer the incoming data for each of the six data streams for further processing, STEP 620.

As described further below, these digitized data streams are supplied to the FPGA 310, which process the data using the downloaded program instructions and criterion to yield an estimate of the instantaneous orientation of the eye coil with respect to the transmitter and receiver coils. Such processing is basically done in two stages.

As the first stage, a demodulator (synchronous, matched-filter, or other type: Van Trees H L. Detection, Estimation and Modulation Theory. Part I—Detection, Estimation and Linear Modulation Theory. John Wiley, Hoboken N.J., 1968) estimates the amplitude of the oscillations. For example, a synchronous demodulator multiplies the incoming damped sinusoid by a reference square wave at the same frequency, and accumulates (integrates) this product over the time of the oscillations, STEPS 630, 640. Because the reference signal has a fixed amplitude, the magnitude of the final result depends on the amplitude of the incoming sinusoid from the resonating coil 114. Such a detection/demodulation scheme is very effective at estimating waveform parameters in a noisy signal.

When the transmitter coil transmits one pulse frequency at a time, only one of the resonating coils of a given search coil assembly is maximally stimulated at a time. However, the other resonating coil of the search assembly can have unavoidable residual stimulation, and the residual ringing of the other coil will be demodulated to some degree. This causes crosstalk between the different resonating coils on the eye. It is possible, to compensate for this crosstalk and essentially eliminate it from the detected signal computationally, because the proportion of signal picked up by each demodulator depends only on the demodulator coefficients. To do this the detectors are run for all of the wireless coil frequencies simultaneously and all of the demodulator outputs are feed into a pre-computed crosstalk correction matrix. The result of multiplying the vector of input values against the crosstalk correction matrix is a corrected vector of demodulated values without crosstalk.

Computing the matrix is straightforward. The frequencies and phases of all of the resonating coils are determined ahead of time, and demodulator parameters are determined for each coil. Once the demodulator parameters are known, the matrix can be computed in software, without the need for further calibration input signals.

For example, for a system with four wireless coils, the demodulators (D1 through D4) would be multiplied by each of the four frequencies (F1 through F4) in turn, yielding the 16 elements of the 4×4 crosstalk output matrix. This matrix is then inverted, and used as the crosstalk correction matrix.

$$CCM = \begin{bmatrix} F1*D1 & F2*D1 & F3*D1 & F4*D1 \\ F1*D2 & F2*D2 & F3*D2 & F4*D2 \\ F1*D3 & F2*D3 & F3*D3 & F4*D3 \\ F1*D4 & F2*D4 & F3*D4 & F4*D4 \end{bmatrix}^{-1}$$

Then, during normal system operation, the outputs of the demodulators (each demodulator output is just the input signal S multiplied by the demodulator coefficients) are multiplied by the CCM to yield the corrected outputs (CO1 through CO4):

$$CCM * \begin{bmatrix} D1*S \\ D2*S \\ D3*S \\ D4*S \end{bmatrix} \Rightarrow \begin{bmatrix} CO1 \\ CO2 \\ CO3 \\ CO4 \end{bmatrix}$$

The second processing stage determines the orientation of the resonating coil from the output of the demodulator, STEPS 650, 660. The intensity of the resonating coil oscillation due to the transmitted pulses depends on the location and angle of the resonating coil being stimulated relative to the transmitter coil 330. Maximum intensity occurs when the resonating and transmitter coils are parallel, and intensity falls off as a function of the sine of the angle between them. Likewise, the received signal intensity depends on the location and angle of the stimulated resonating coil relative to the receiver coil 340, again as a function of the sine of the angle. Thus, for transmitter and receiver coils fixed to the head, the amplitude of the received signal (output of the demodulator) depends on the squared sine of the angle of the eye coil and hence of the eye. Derivation of this location and angle is done in the FPGA 310, more specifically in the downloaded program in the FPGA or in associated processing hardware (DSP or microprocessor).

The basic principle behind measurement of eye movements in three dimensions (horizontal, vertical, torsional) stems from the fact that two different resonating coils with two different resonant frequencies and approximately orthogonal to each other can be embedded in the search coil assembly 100. The so-called "torsion" resonating coil is wound essentially in a fore-aft direction on or in the support member. Each of these two coils can then be individually stimulated by a set of transmitter pulses, where the coil that is stimulated is the one that has a resonant frequency that matches the repetition frequency of the transmitter pulses. The oscillations in the resonant eye coil are allowed to decay, and then another set of transmitter pulses is generated at the resonant frequency of the other eye coil. This sequence is repeated rapidly enough that a set of four total resonating coils (two in each eye) can be stimulated sequentially in much less than 1 ms, which allows a sample rate for the eye movements of 1 KHz or better. Proper design of the transmitter pulse rate also enables all resonating coils to be stimulated simultaneously, allowing for synchronous measurements of all position and orientation parameters.

Figure 5:
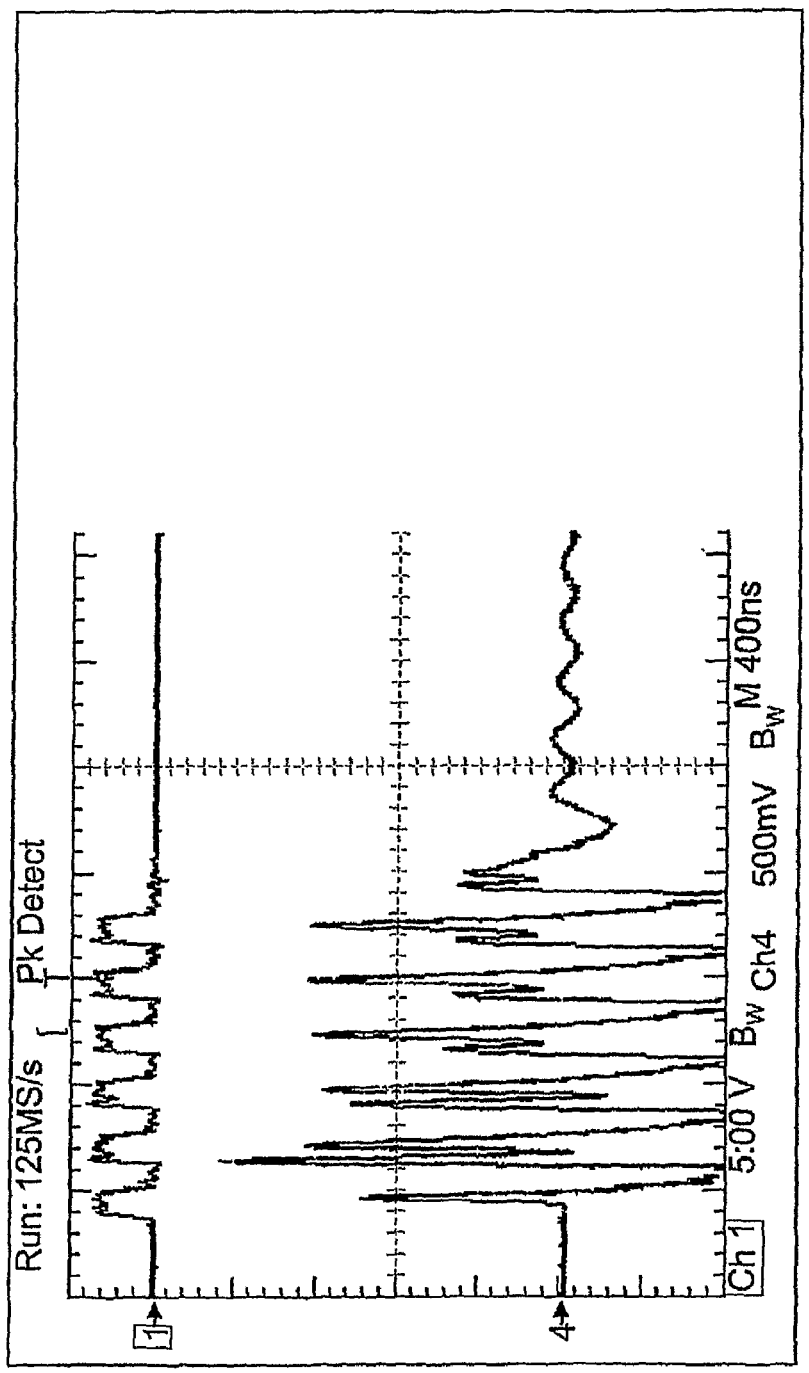
FIG. 5 is an illustrative of a digital oscilloscope screen showing the transmitted pulses and the oscillation from the resonating coil after reception by the receiver coil, filtering and amplification.
Figure 6:
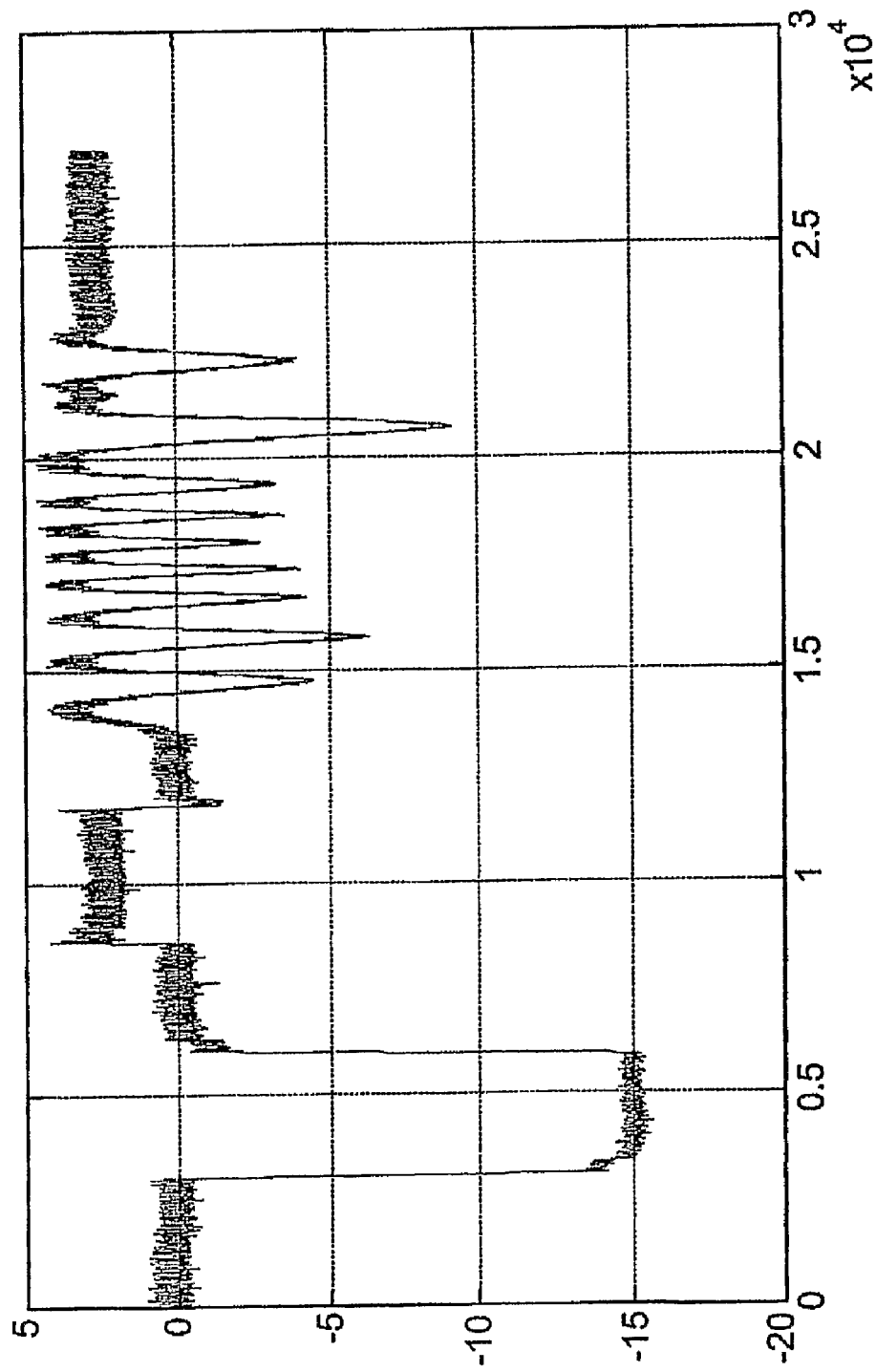
FIG. 6 is a graphical representation of the demodulator output in which the subject looked at targets which was followed by active head movement.

There is shown in FIGS. 5-6 a set of sample data demonstrating the operation of a wireless search coil and related system of the present invention. FIG. 5 is presents a digital oscilloscope screen showing the transmitted pulses (top) and the oscillation from the resonating coil after reception by the receiver coil, filtering and amplification (bottom). FIG. 6 is a graphical representation of the demodulator output (i.e., eye angle), while the test subject fixated targets at various locations and then moved the head sinusoidally while maintaining gaze on a single point. In particular, the subject looked at targets centered, 5 degrees to the right and 15 degrees to the left followed by active head movements.

Figure 7:
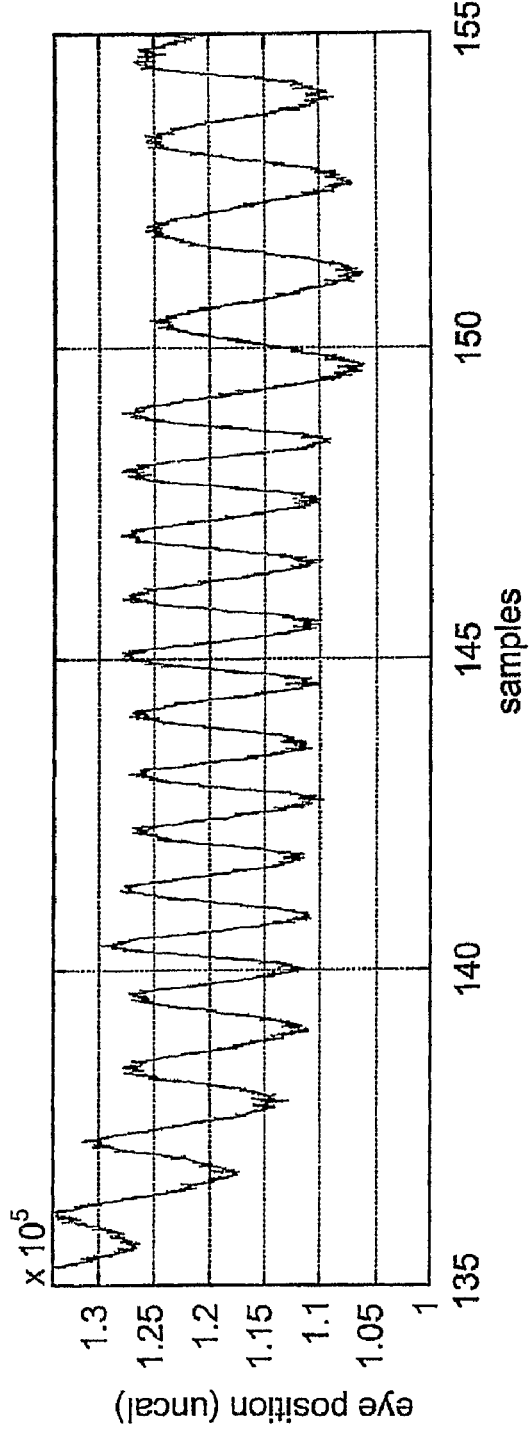
FIGS. 7-8 are graphical views illustrating wireless coil data obtaining in "weightless" parabolic flight aboard a research aircraft.
Figure 8:
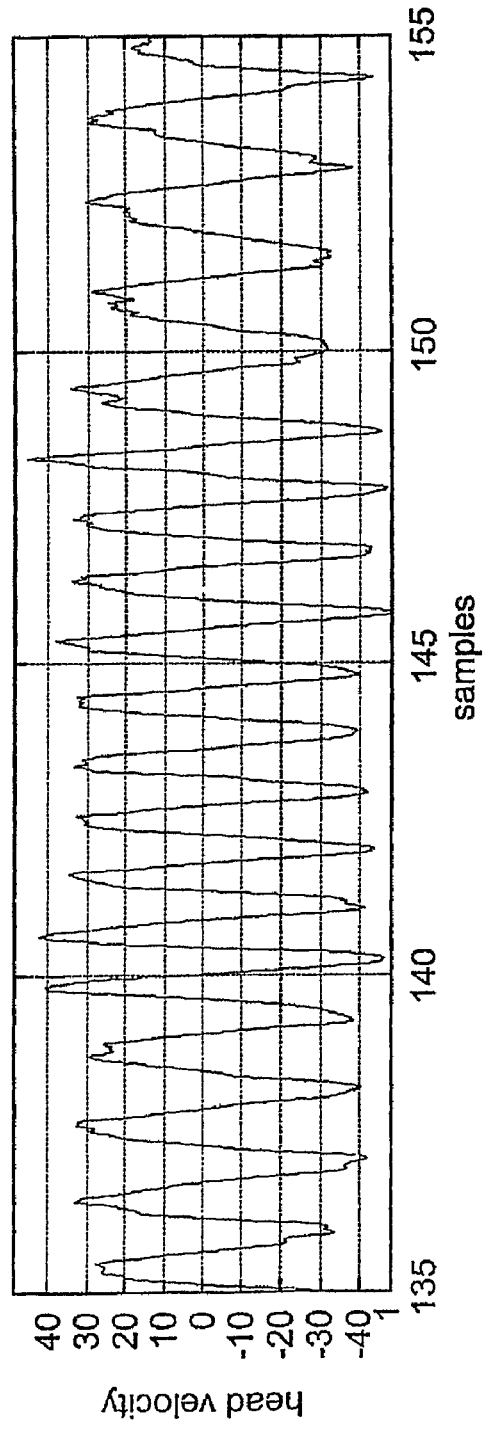

There is shown in FIGS. 7-8 some illustrative wireless coil data obtaining in "weightless" parabolic flight aboard a research aircraft. The subject was performing pitching head motions in the zero-g portion of flight and compensatory eye movements are generated to compensate for head motion. FIG. 7 is a graphical view of the vertical eye position using a wireless search coil according to the present invention and FIG. 8 is a graphical view illustrating the pitch rotational head velocity from rate sensor attached to a biteboard held in the subject's mouth.

Although a preferred embodiment(s) of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A wireless scleral search device for use in detecting and measuring eye movement; said wireless scleral search device comprising:
    a support member, one surface of which is shaped to facilitate locating the support member on an eye, wherein the support member is configured so that it moves with movement of the eye;
    a resonating coil being mounted to said support member so as to extend about a circumference of the support member and wherein said resonating coil is configured such that when it is mounted to said support member elements thereof do not extend outwardly from the support member; and
    wherein the resonating coil is configured so that signals at a resonance frequency are induced in the coil from externally supplied signals and so such resonance frequency signals are outputted by the resonance coil.

2. The wireless scleral search device of claim 1, wherein the resonating coil is configured to form a resonant coil-capacitor combination, where the capacitance and inductance of the coil are such as to resonate at a desired frequency.

3. The wireless scleral search device of claim 1, wherein the resonating coil is disposed within the support member.

4. The wireless scleral search device of claim 1, wherein the support member is formed of a bio-compatible material.

5. The wireless scleral search device of claim 1, further comprising a capacitor that is operably coupled to said resonating coil.

6. The wireless scleral search device of claim 1, further comprising:
a second resonating coil that is mounted to said support member so as to be concentric with the resonating coil that extends about a circumference of the support member and wherein said resonating coil and said second resonating coil are configured such that when they are mounted to said support member, elements of both resonating coils do not extend outwardly from the support member.

7. The wireless scleral search device of claim 1, wherein the resonating coil is configured so as to generally approximate a cross-sectional contour of the support member.

8. A wireless scleral search device for use in detecting and measuring eye movement; said wireless scleral search device comprising:
a support member, one surface of which is shaped to facilitate locating the support member on an eye wherein the support member is configured so that it moves with movement of the eye;
a first resonating coil and a second resonating coil, each coil being mounted to said support member so that each coil extends about a circumference of the support member and so that the coil moves with the movement of the support member and wherein each of said first and second coils is configured so elements thereof do not extend outwardly from the support member; and
wherein the first and second resonating coils are configured so that signals at a resonance frequency are induced in the coil from externally supplied signals and so such resonance frequency signals are outputted by the resonance coil.

9. The wireless scleral search device of claim 8, wherein the first resonating coil and the second resonating coil are mounted to and arranged on the support member such that the first resonating coil and the second resonating coil so the search device can be used to detect and measure horizontal, vertical and torsional eye movement.

10. The wireless scleral search device of claim 8, wherein the first and second resonating coils are configured to form a resonant coil-capacitor combination, where the capacitance and inductance of each coil are such as to resonate at a desired frequency.

11. The wireless scleral search device of claim 8, wherein the first resonating coil and the second resonating coil are configured so that the coils resonant at different frequencies.

12. The wireless scleral search device of claim 8, wherein the first and second resonating coils are disposed within the support member.

13. The wireless scleral search device of claim 8, wherein the support member is formed of a bio-compatible material.

14. The wireless scleral search device of claim 8, further comprising at least one capacitor, wherein said at least one capacitor is operably coupled to one of said first resonating coil and said second resonating coil.

15. The wireless scleral search device of claim 8, wherein said second resonating coil is concentric with said first resonating coil.

16. The wireless scleral search device of claim 8, wherein each of said first and second resonating coils is configured so as to generally approximate a cross-sectional contour of the support member.

17. A system for detecting and measuring eye movement; said system including:
a coil assembly, said coil assembly including:
a support member, one surface of which is shaped to facilitate locating the support member on an eye and so that the support member moves with eye movement, and
at least one resonating coil being mounted to said support member such that the coil moves with movement of the support member and wherein said at least one resonating coil is configured such that elements thereof do not extend outwardly from the support member, where the resonating coil also is configured so that signals at a resonance frequency are outputted by the resonating coil;
a transmitting apparatus including at least one antenna, the transmitting apparatus being configured so as to periodically output a signal(s) that is induced in the eye coil so as to cause resonance of the at least one resonating coil, and where the at least one antenna is disposed in a predetermined manner with respect to the coil assembly;
a signal receiving apparatus, the signal reception apparatus being configured to receive a resonance signal(s) from the at least one resonating coil during a quiescent period between periodic signals outputted by the transmitting apparatus, and wherein the receiving apparatus includes at least a plurality of antennas that are arranged in groups that are orthogonal to each other; and
a measurement determining apparatus, operably coupled to the signal receiving apparatus so as to determine a measurement corresponding to one of a horizontal, vertical or torsional movement of the eye.

18. The detecting and measuring system of claim 17, wherein the resonating coil is configured to form a resonant coil-capacitor combination, where the capacitance and inductance of the coil are such as to resonate at a desired frequency.

19. The detecting and measuring system of claim 17, wherein the resonating coil is disposed within the support member.

20. The detecting and measuring system of claim 17, further comprising a control apparatus being operably coupled to each of the transmitting apparatus and the receiving apparatus to synchronize operation of the transmitting and receiving apparatus.

21. The detecting and measuring system of claim 20, wherein:
the receiving apparatus further includes a receiver; and
the control apparatus is configured to control the receiving apparatus so that each of the at least a plurality of antennas is operably coupled to the receiver during a signal quiescent period of the transmitting apparatus.

22. The detecting and measuring system of claim 21, wherein the at least a plurality of antennas are disposed with respect to the coil assembly such that the measurement determining apparatus can determine a measurement corresponding to one of a horizontal, vertical or torsional rotational movement of the eye.

23. The detecting and measuring system of claim 21, wherein the at least a plurality of antennas are with respect to the coil assembly such that the measurement determining apparatus can determine a measurement corresponding to horizontal and vertical translational movement of the eye.

24. The detecting and measuring system of claim 23, wherein the receiving apparatus further includes N antennas, N being an integer greater than or equal to 3, wherein disposition of each of the N antennas with respect to the coil assembly is set such that the measurement determining apparatus can determine a measurement corresponding to horizontal, vertical and torsional rotational movement of the eye.

25. The detecting and measuring system of claim 17, wherein said coil assembly further includes a capacitor that is operably coupled to said at least one resonating coil.

26. The detecting and measuring system of claim 17, wherein said coil assembly further includes a second resonating coil that is mounted to said support member so as to be concentric with the resonating coil that extends about a circumference of the support member and wherein said resonating coil and said second resonating coil are configured such that when they are mounted to said support member, elements of both resonating coils do not extend outwardly from the support member.

27. The detecting and measuring system of claim 17, wherein said at least one resonating coil is configured so as to generally approximate a cross-sectional contour of the support member.

28. The detecting and measuring system of claim 17, wherein the signal receiving apparatus further includes three antennas that are arranged so as to be orthogonal to each other.

29. The detecting and measuring system of claim 17, wherein the signal receiving apparatus further includes X sets of three antennas, where X is greater than or equal to two and where the three antennas are arranged so as to be orthogonal to each other.

30. The detecting and measuring system of claim 29, where X is greater than or equal to three.

31. A method for measuring eye movement comprising the steps of:
  providing a resonating coil assembly including a resonating coil and an array of two or more receiver coils, the two or more receiver coils being are arranged so as to be orthogonal to each other;
  disposing the resonating coil on an eye so that it moves with eye movement;
  stimulating the resonating coil so the coil continues to output signals after such stimulating is terminated;
  detecting and processing the signals being outputted by the resonating coil in a time sequence following termination of the stimulating;
  determining one of the position or orientation of the eye from the detected and processed signals.

32. The method for measuring eye movement of claim 31, wherein said stimulating includes transmitting a sequence of pulses at a predetermined frequency to stimulate the resonating coil.

* * * * *